United States Patent
Ailinger et al.

(10) Patent No.: US 11,647,896 B2
(45) Date of Patent: May 16, 2023

(54) ROLLERLESS TUBULAR CONNECTOR FOR TRANSFERRING ROTATIVE FORCE FROM INSERTION SECTION OF ENDOSCOPE TO SPIRAL TUBE

(71) Applicant: OLYMPUS CORPORATION, Tokyo (JP)

(72) Inventors: Robert E. Ailinger, Norwood, MA (US); David Gately, Maynard, MA (US); Matthew S. Carlone, Marlborough, MA (US)

(73) Assignee: OLYMPUS CORPORATION, Tokyo (JP)

( * ) Notice: Subject to any disclaimer, the term of this patent is extended or adjusted under 35 U.S.C. 154(b) by 543 days.

(21) Appl. No.: 16/367,657

(22) Filed: Mar. 28, 2019

(65) Prior Publication Data
US 2020/0305687 A1    Oct. 1, 2020

(51) Int. Cl.
*A61B 1/00* (2006.01)
*A61B 1/005* (2006.01)

(52) U.S. Cl.
CPC ........ *A61B 1/00154* (2013.01); *A61B 1/0016* (2013.01); *A61B 1/0057* (2013.01); *A61B 1/00066* (2013.01); *A61B 1/00121* (2013.01); *A61B 1/00148* (2022.02); *A61B 1/00156* (2013.01); *A61B 1/00133* (2013.01)

(58) Field of Classification Search
None
See application file for complete search history.

(56) References Cited

U.S. PATENT DOCUMENTS

| 5,217,002 | A | * | 6/1993 | Katsurada | ............ | A61B 1/0011 |
| | | | | | | 600/182 |
| 5,288,556 | A | | 2/1994 | Lemelson | | |
| 5,601,537 | A | * | 2/1997 | Frassica | .............. | A61J 15/0046 |
| | | | | | | 604/517 |
| 5,989,230 | A | * | 11/1999 | Frassica | ................ | A61F 2/0009 |
| | | | | | | 604/510 |

(Continued)

FOREIGN PATENT DOCUMENTS

| DE | 196 25 892 A1 | 1/1997 |
| EP | 2 896 346 A1 | 7/2015 |

(Continued)

OTHER PUBLICATIONS

International Search Report dated Jun. 18, 2020 together with the Written Opinion received in related International Application No. PCT/JP2020/013853.

*Primary Examiner* — Ryan N Henderson
(74) *Attorney, Agent, or Firm* — Scully, Scott, Murphy & Presser, P.C.

(57) ABSTRACT

A tubular connector for use with a spiral tube used on an insertion section of an endoscope. The tubular connector including: an outer surface; an inner surface; and a plurality of cams circumferentially spaced on the inner surface to project radially inward from the inner surface, the plurality of cams extending in a longitudinal direction of the tubular connector; wherein each of the plurality of cams have one or more cam surfaces configured to engage a rotating member to rotate the spiral tube. The plurality of cams can alternatively be formed directly on an interior surface of the spiral tube.

15 Claims, 4 Drawing Sheets

(56) References Cited

U.S. PATENT DOCUMENTS

| | | | | |
|---|---|---|---|---|
| 6,379,334 B1* | 4/2002 | Frassica | A61B 1/0016 | 604/165.01 |
| 7,048,717 B1* | 5/2006 | Frassica | A61M 25/0021 | 604/165.01 |
| 7,621,867 B2* | 11/2009 | Kura | A61B 1/04 | 439/23 |
| 7,637,864 B2* | 12/2009 | Yokoi | A61B 1/00156 | 600/114 |
| 7,780,650 B2* | 8/2010 | Frassica | A61M 25/0021 | 600/105 |
| 7,806,888 B2* | 10/2010 | Frassica | A61B 1/0016 | 600/109 |
| 7,862,504 B2* | 1/2011 | Kura | A61B 1/00148 | 600/137 |
| 7,909,799 B2* | 3/2011 | Frassica | A61B 1/00128 | 604/165.04 |
| 7,938,772 B2* | 5/2011 | Kura | A61B 1/00156 | 600/137 |
| 7,951,068 B2* | 5/2011 | Kura | A61B 1/0016 | 600/137 |
| 8,177,709 B2* | 5/2012 | Uchiyama | A61B 1/01 | 600/114 |
| 8,235,942 B2* | 8/2012 | Frassica | A61B 17/12159 | 600/101 |
| 8,277,374 B2* | 10/2012 | Tsumaru | A61B 1/31 | 600/116 |
| 8,317,678 B2* | 11/2012 | Frassica | A61M 25/0068 | 600/101 |
| 8,343,040 B2* | 1/2013 | Frassica | A61M 25/0105 | 600/137 |
| 8,366,674 B2* | 2/2013 | Frassica | A61B 1/00154 | 600/105 |
| 8,414,477 B2* | 4/2013 | Tallarida | A61M 25/0105 | 600/137 |
| 8,435,229 B2* | 5/2013 | Frassica | A61M 25/0105 | 604/528 |
| 8,491,466 B2* | 7/2013 | Okada | A61B 1/2736 | 600/101 |
| 8,500,628 B2* | 8/2013 | Frassica | A61B 1/12 | 600/110 |
| 8,574,220 B2* | 11/2013 | Frassica | A61M 25/0017 | 600/137 |
| 9,538,904 B2* | 1/2017 | Ailinger | G02B 23/2476 | |
| 9,622,648 B2* | 4/2017 | Naito | A61B 1/0016 | |
| 9,829,080 B2* | 11/2017 | Ishizaki | F16H 7/02 | |
| 9,895,051 B2* | 2/2018 | Nishiie | A61B 1/00112 | |
| 10,299,659 B2* | 5/2019 | Ishizaki | G02B 23/2476 | |
| 2002/0045855 A1* | 4/2002 | Frassica | A61B 1/0008 | 604/103.08 |
| 2003/0020810 A1* | 1/2003 | Takizawa | A61B 34/73 | 348/61 |
| 2004/0243108 A1* | 12/2004 | Suzuki | F16C 1/02 | 606/1 |
| 2005/0251108 A1* | 11/2005 | Frassica | A61B 1/00154 | 600/101 |
| 2005/0272976 A1* | 12/2005 | Tanaka | A61B 1/0016 | 600/114 |
| 2006/0063974 A1* | 3/2006 | Uchiyama | A61B 1/041 | 600/128 |
| 2006/0169293 A1* | 8/2006 | Yokoi | A61B 1/00158 | 128/899 |
| 2006/0206002 A1* | 9/2006 | Frassica | A61B 1/00148 | 600/101 |
| 2006/0270901 A1* | 11/2006 | Bern | A61B 1/0016 | 600/101 |
| 2007/0005041 A1* | 1/2007 | Frassica | A61M 25/04 | 623/1.1 |
| 2007/0038021 A1* | 2/2007 | Kura | A61B 1/00156 | 600/101 |
| 2007/0055097 A1* | 3/2007 | Kura | A61B 1/31 | 600/101 |
| 2007/0059956 A1* | 3/2007 | Kura | A61B 1/00154 | 439/131 |
| 2007/0059989 A1* | 3/2007 | Kura | A61B 1/31 | 439/685 |
| 2007/0060790 A1* | 3/2007 | Kura | A61B 1/31 | 600/114 |
| 2007/0066104 A1* | 3/2007 | Kura | A61B 1/0607 | 439/157 |
| 2007/0161862 A1* | 7/2007 | Yokoi | A61B 1/00158 | 600/113 |
| 2007/0167674 A1* | 7/2007 | Toyama | A61B 1/31 | 600/101 |
| 2007/0167684 A1* | 7/2007 | Toyama | A61B 1/0016 | 600/128 |
| 2007/0299301 A1* | 12/2007 | Uchiyama | A61B 34/73 | 600/101 |
| 2008/0009675 A1* | 1/2008 | Kura | A61B 1/0016 | 600/128 |
| 2008/0033245 A1* | 2/2008 | Kura | A61B 1/00148 | 600/114 |
| 2008/0086029 A1* | 4/2008 | Uchiyama | A61B 1/00148 | 600/114 |
| 2008/0183033 A1* | 7/2008 | Bern | A61B 1/00148 | 600/101 |
| 2008/0188710 A1* | 8/2008 | Segawa | A61B 1/041 | 600/101 |
| 2008/0262305 A1* | 10/2008 | Omoto | A61B 1/00154 | 600/118 |
| 2009/0005645 A1* | 1/2009 | Frassica | A61B 17/12022 | 600/137 |
| 2009/0012359 A1* | 1/2009 | Tanaka | A61B 1/00158 | 600/114 |
| 2009/0023994 A1* | 1/2009 | Kura | A61B 1/31 | 600/114 |
| 2009/0030277 A1* | 1/2009 | Fujimoto | A61B 1/00071 | 600/114 |
| 2009/0118582 A1* | 5/2009 | Tsumaru | A61B 1/00094 | 600/114 |
| 2009/0156897 A1* | 6/2009 | Omot | A61B 1/005 | 600/118 |
| 2009/0171152 A1* | 7/2009 | Aoki | G02B 23/2476 | 600/114 |
| 2009/0209812 A1* | 8/2009 | Omoto | A61B 1/00156 | 600/110 |
| 2009/0281384 A1* | 11/2009 | Tsumaru | A61B 1/00148 | 600/114 |
| 2009/0281387 A1* | 11/2009 | Takizawa | A61B 1/00158 | 600/117 |
| 2011/0144434 A1* | 6/2011 | Okada | A61B 1/00156 | 600/114 |
| 2011/0307069 A1* | 12/2011 | Frassica | A61B 1/0008 | 606/127 |
| 2011/0319713 A1* | 12/2011 | Frassica | A61B 1/00148 | 600/114 |
| 2012/0004504 A1* | 1/2012 | Frassica | A61M 27/008 | 600/114 |
| 2012/0029281 A1* | 2/2012 | Frassica | A61B 1/00156 | 600/114 |
| 2013/0035552 A1* | 2/2013 | Moriyama | A61B 1/31 | 600/149 |
| 2014/0058203 A1* | 2/2014 | Naito | G02B 23/2476 | 600/137 |
| 2014/0296771 A1* | 10/2014 | Naito | A61B 1/00156 | 604/19 |
| 2014/0303440 A1* | 10/2014 | Nishiie | A61B 1/00071 | 600/114 |
| 2014/0330079 A1* | 11/2014 | Ishizaki | A61B 1/00128 | 600/114 |
| 2015/0133856 A1* | 5/2015 | Nishiie | A61B 1/00135 | 604/95.01 |

(56) References Cited

U.S. PATENT DOCUMENTS

2017/0071447 A1* 3/2017 Nishiie .............. A61B 1/00071
2017/0279237 A1* 9/2017 Ishizaki ............. A61B 1/00148
2019/0000303 A1   1/2019 Suzuki et al.

FOREIGN PATENT DOCUMENTS

EP     3 216 382 A1    9/2017
WO    2018/185470 A2   10/2018

* cited by examiner

ROLLERLESS TUBULAR CONNECTOR FOR TRANSFERRING ROTATIVE FORCE FROM INSERTION SECTION OF ENDOSCOPE TO SPIRAL TUBE

BACKGROUND

1. Field

The present disclosure relates generally to a rotating force transmission connector and more particularly to a rollerless tubular connector for transferring a rotative force from an insertion section of an endoscope to a spiral tube rotatably disposed on the insertion section.

2. Prior Art

In general, an insertion section of an insertion apparatus, such as an endoscope, is inserted into, for example, a lumen. One type of such an endoscope inserted into a lumen which is known is a self-propelled insertion apparatus.

In such a rotary self-propelled insertion apparatus, a rotating cylindrical body called a spiral tube is provided, on which a spiral fin is formed on a thin-walled tube. The spiral tube is rotatably disposed on an outer circumferential face of an insertion section of the endoscope. When the spiral tube rotates, the spiral fin contacts an inner wall of the lumen, thus generating a propulsion force. By this propulsion force, the insertion section is propelled in a direction of insertion or in a direction of removal.

Conventional spiral tubes utilize two sets of rollers to be rotated around the insertion portion of the endoscope. A first set of rollers are driven by a motor and are internal to the endoscope insertion portion. A second set of rollers are provided on an internal portion of the spiral tube, are engaged with the first set of rollers and transfer a rotative force from the motor and first set of rollers to the second set of rollers to rotate the spiral tube. A water-tight cover is disposed between the first and second sets of rollers and attached to the endoscope insertion portion to maintain a water tight condition in the endoscope insertion section. Such second set of rollers are either provided directly on the internal surface of the spiral tube or on an internal surface of a connector fastened to the internal surfaces of the spiral tube. The second set of bearings are generally machined steel roller bearings and require a precision molded bearing retaining collar for placement of the same, as well as associated inspection and assembly costs, which make up a significant total cost for the spiral tube, which is generally a disposable item.

SUMMARY

Accordingly, a tubular connector for use with a spiral tube is provided. The tubular connector comprising: an outer surface; an inner surface; and a plurality of cams circumferentially spaced on the inner surface to project radially inward from the inner surface, the plurality of cams extending in a longitudinal direction of the tubular connector; wherein each of the plurality of cams have one or more cam surfaces configured to engage a rotating member to rotate the spiral tube.

The plurality of cams can be formed of a material different from a material forming other portions of the tubular connector.

At least the one or more cam surfaces of the plurality of cams can be configured to be coated with a material different from a material forming other portions of the tubular connector.

At least the one or more cam surfaces of the plurality of cams can be configured to be formed of a material different from a material forming other portions of the plurality of cams.

Also provided is a spiral tube for use with an endoscope insertion section having a rotating member. The spiral tube comprising: a tube; a spiral fin disposed on an exterior surface of the tube; and a plurality of cams circumferentially spaced to project radially inward from an inner surface of the tube, the plurality of cams extending in a longitudinal direction of the tubular connector; wherein each of the plurality of cams have one or more cam surfaces configured to engage the rotating member to rotate the spiral tube.

The spiral tube can further comprise a tubular connector having the plurality of cams, the tubular connector being fixed to the inner surface of the tube. The plurality of cams can be formed of a material different from a material forming other portions of the tubular connector. At least the one or more cam surfaces of the plurality of cams can be configured to be coated with a material different from a material forming other portions of the tubular connector. At least the one or more cam surfaces of the plurality of cams can be configured to be formed of a material different from a material forming other portions of the plurality of cams.

Still further provided is an endoscope system comprising: an endoscope having an elongated insertion section, the insertion section having a rotating member; a spiral tube rotatably disposed on the insertion section, the spiral tube comprising: a tube; a spiral fin disposed on an exterior surface of the tube; and a plurality of cams circumferentially spaced to project radially inward from an inner surface of the tube, the plurality of cams extending in a longitudinal direction of the tubular connector; wherein each of the plurality of cams have one or more cam surfaces configured to engage the rotating member to rotate the spiral tube.

The endoscope system can further comprise a tubular connector having the plurality of cams, the tubular connector being fixed to the inner surface of the tube. The plurality of cams can be formed of a material different from a material forming other portions of the tubular connector. At least the one or more cam surfaces of the plurality of cams can be configured to be coated with a material different from a material forming other portions of the tubular connector. At least the one or more cam surfaces of the plurality of cams can be configured to be formed of a material different from a material forming other portions of the plurality of cams.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

While the disclosed embodiments have particular utility for use with transmitting a rotative force from an insertion section to a spiral tubes rotatable disposed on the insertion section of an endoscope and are described below with regard to the same, the apparatus and methods disclosed herein are not so limited and have utility to other types of tubular connectors for transmitting a rotative force from one member to another through the tubular connector.

Figure 1:
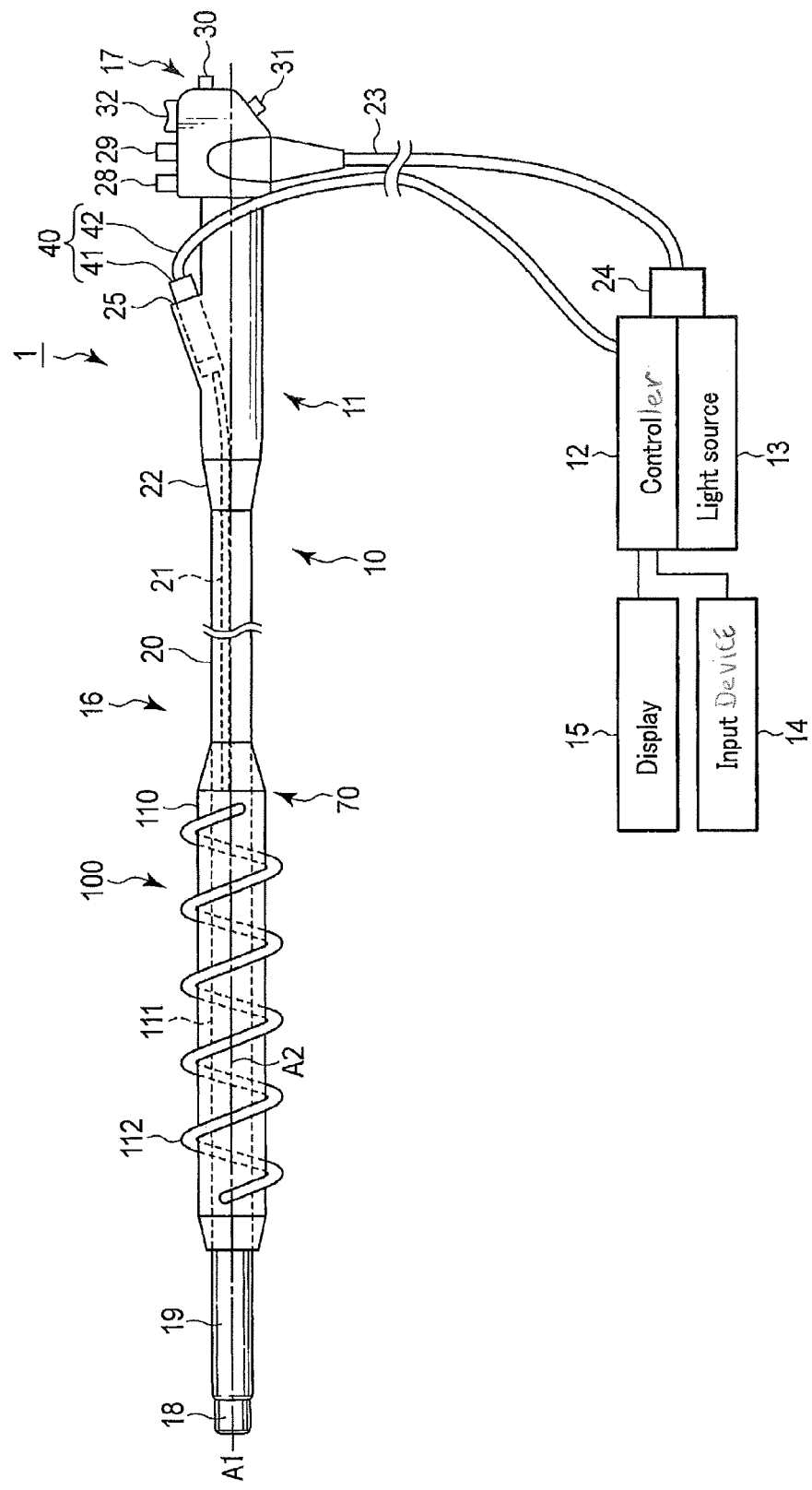
FIG. 1 schematically illustrates an endoscope system having a spiral tube rotatably disposed on an insertion section of an endoscope.

FIG. 1 schematically shows an endoscope apparatus 1 comprising an endoscope system 10 including an endoscope 11, and a spiral tube 100 which is rotatably disposed on the insertion section 16 of the endoscope 11. The endoscope 11 is inserted into an insertion object (for example, a serpentine intestinal canal such as a large intestine and a small intestine). The spiral tube 100 assists the endoscope 11 to be inserted into the insertion object. The endoscope system 10 comprises an endoscope 11, a controller 12, a light source 13, an input device 14, and a display 15.

The endoscope 11 comprises an insertion section 16 which is inserted into a lumen, and an operation section 17 provided on a proximal end side of the insertion section 16. The insertion section 16 is an elongated tubular body at a distal end side of the endoscope, and extends in a longitudinal axis direction. The insertion section 16 comprises a distal rigid portion 18, a bending portion 19 provided on the proximal end side of the distal rigid portion 18, and a flexible tube portion 20 provided on the proximal end side of the bending portion 19. In the distal rigid portion 18, an unillustrated illumination optical system, observation system, and image sensor, etc. are contained. The bending portion 19 is bent in a desired direction by a user controlling the operation section 17. The flexible tube portion 20 is free to bend, and, for example, bends along the bent shape inside the lumen, into which the insertion section 16 is inserted. Furthermore, inside the insertion section 16 extends a channel 21 for inserting therethrough a drive shaft 51 explained below.

The operation section 17 is connected to the flexible tube portion 20 by a stopper 22. Across the inside of the insertion section 16 to the operation section 17 extends an optical fiber whose distal end is connected to the illumination optical system of the distal rigid portion 18 and an electric cable whose distal end is connected to the image sensor of the distal rigid portion 18, etc. These optical fibers and electric cables are accommodated in a universal cord 23 extending from the proximal end side of the operation section 17. At the proximal end of the universal cord 23 is provided a scope connector 24. The universal cord 23 is connected to the controller 12 and the light source 13 via the scope connector 24. The operation section 17 is also provided with a driving source attachment port 25 communicating with the channel 21 inside the insertion section 16.

The controller 12 is electrically connected to the endoscope 11, the light source 13, the input device 14, and the display 15. The controller 12 controls the operations of the endoscope 11 and peripheral device connected thereto (for example, the light source 13 and the later explained driving source 40). The controller 12 also includes an image processor (not shown). The light source 13 supplies illumination light to the illumination optical system arranged in the distal rigid portion 18 via the optical fiber. The input device 14 is used by a user to input various instructions to the endoscope 11, etc. The display 15 displays an image obtained by the image sensor of the distal rigid portion 18 and processed by the controller 12, as well as operation information of the endoscope, etc.

Figure 2:
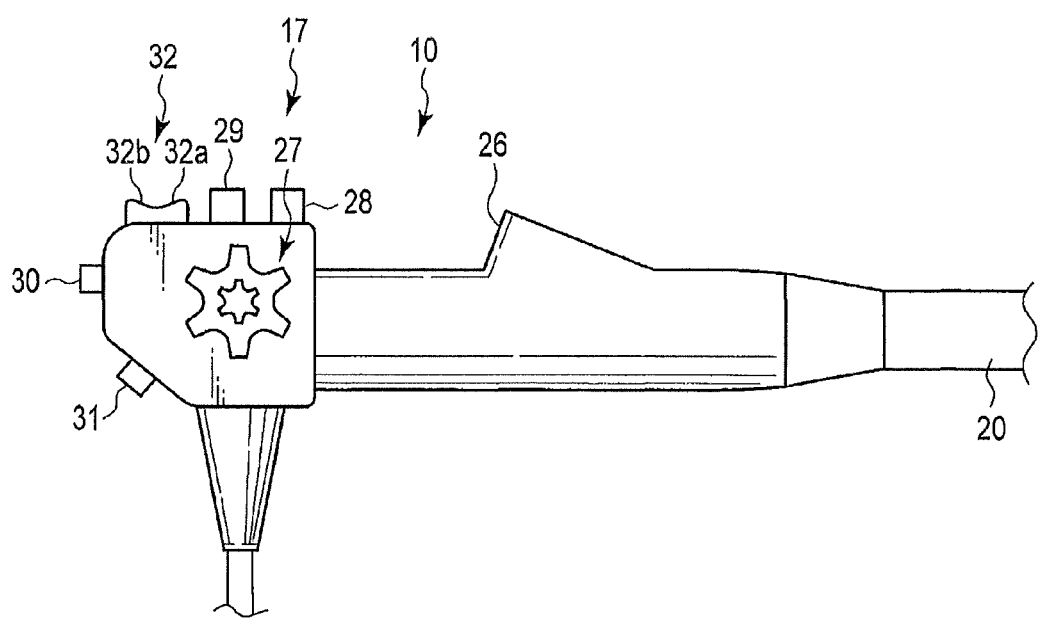
FIG. 2 illustrates a side surface of an operation section of the endoscope shown in FIG. 1.

FIG. 2 shows a side surface of a side of the operation section 17 of the endoscope 11 that is opposite to the side shown in FIG. 1. The operation section 17 comprises a treatment tool insertion port 26 communicating with an treatment tool channel (not shown) extending inside the insertion section 16. The treatment tool insertion port 26 is arranged side by side with the driving source attachment port 25 shown in FIG. 1. Treatment tools such as an ultrasonic probe or biopsy forceps are inserted in the treatment tool insertion port 26.

As shown in FIG. 2, on the side surface of the operation section 17 is provided a bending operation knob 27 to which an operation for bending the bending portion 19 in a desired direction is input. In the inside of the operation section 17, a proximal end of an bending wire (not shown) for bending the bending portion 19 is connected to a shaft connected to the bending operation knob 27. The distal end of the bending wire is connected to the distal end portion of the bending portion 19. When a user rotates the bending operation knob 27, the bending wire connected thereto is pulled and causes the bending portion 19 to bend.

The operation section 17 is provided with various switches 28, 29, 30, and 31 such as an air feed/water feed switch, a suction switch, a photographing switch, and a change-over switch for switching over other predetermined functions. Furthermore, the operation section 17 is provided with a rotation operation input switch 32 to output to the controller 12 a signal for rotating the spiral tube 100 around a center axis A1 of the insertion section 16. The rotation operation input switch 32 outputs a signal for causing the spiral tube 100 to rotate in a first direction (for example, clockwise) when a user, for example, presses a position indicated by reference numeral 32a, and outputs to the control unit 12 a signal for causing the spiral tube 100 to rotate in a second direction (for example, counter-clockwise) which is opposite to the first direction when a position indicated by reference numeral 32b is pressed.

With reference to FIG. 1 again, on the driving source attachment port 25 is attached a driving source 40 for causing the spiral tube 100 to rotate and drive around the center axis A1. The driving source 40 comprises a motor main body 41 which comprises a rotary shaft and a motor cable 42 which extends from the motor main body 41. The outer periphery of the motor main body 41 is retained on the driving source attachment port 25 by a retaining ring (not shown). The rotary shaft of the motor main body 41 is connected to the drive shaft 51 explained below. The proximal end of the motor cable 42 is electrically connected to the controller 12.

The spiral tube 100 will be explained below with regard to FIG. 1. The spiral tube 100 comprises a cylindrical tube main body 110. The tube main body 110 is a disposable tube which is detachably attached on the outer periphery of the insertion section 16. The tube main body 110 extends along a longitudinal axis A2. The longitudinal axis A2 is coaxial with the above-mentioned rotation center axis A1 when the tube main body 110 is attached to the insertion section 16.

The tube main body 110 is provided with a lumen 111 through which the insertion section 16 may be inserted across the entire length.

The tube main body 110 is a flexible tube which is formed by a resin material, such as polyurethane. On at least a part of the outer periphery of the tube main body 110 is formed a spiral fin 112 which is provided spirally clockwise as viewed in the proximal end direction. The spiral fin 112 is fixed to the tube main body 110 by adhesion or welding, etc., or is formed integrally with the tube main body 110, and protrudes in a radial direction from the outer periphery of the tube main body 110. The spiral fin 112 is formed of, for example, polyurethane, TPE, silicon, etc.

Figure 3:
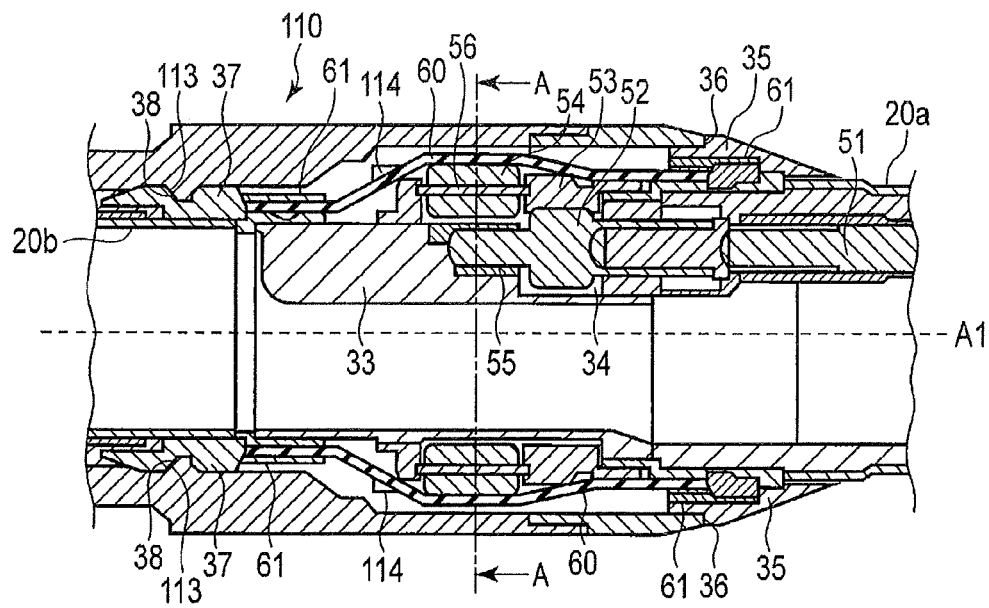
FIG. 3 shows a cross-section in a longitudinal axis direction including a connector for transferring a rotative force from the insertion section to the spiral tube.
Figure 4:
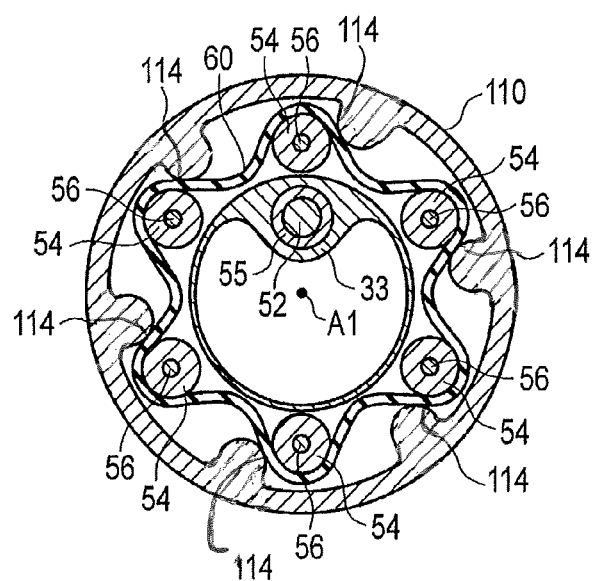
FIG. 4 illustrates a cross-sectional view taken along line A-A in FIG. 3.

The attachment of the tube main body 110 of the spiral tube 100 to the insertion section 16 (flexible tube portion 20) regarding a driving force transmission mechanism 70 will be explained below with regard to FIG. 3, which shows a cross-section including the driving force transmission mechanism 70 for rotating and driving the tube main body 110 of the spiral tube 100 in a longitudinal axis direction. FIG. 4 is a cross-sectional view taken along line A-A in FIG. 3. As shown in FIG. 3, the flexible tube portion 20 has a first flexible tube portion 20a, and a second flexible tube portion 20b which is closer to the proximal end side of the flexible tube portion 20 than the first flexible tube portion 20a. The first flexible tube portion 20a and the second flexible tube portion 20b are connected by a rigid base portion 33 arranged therebetween. The base portion 33 forms a cavity 34 therein at the insertion section 16.

On the outer periphery of the base portion 33 is provided a stopper member 35. On the stopper member 35 is formed a receiving surface 36 to which the proximal end portion of the tube main body 110 abuts. This prevents the tube main body 110 from moving to the proximal end side when the tube main body 110 is attached to the insertion section 16. Furthermore, on the outer periphery of the base portion 33 is provided an annular engagement member 37 on which an annular groove 38 is formed. On the tube main body 110 is provided a pawl 113 which engages with the groove 38. When the tube main body 110 is attached to the insertion section 16, by engaging the groove 38 with the pawl 113, the movement of the tube main body 110 in the longitudinal direction is regulated.

On the insertion section 16 of the endoscope 11 is provided a flexible drive shaft 51, a rotation gear 52, an internal gear 53, and an internal roller 54 (rotating members) with a circumferential surface. In FIG. 4, six internal rollers 54 are shown. However, the number of rollers is not limited to six.

As shown in FIG. 1, the proximal end of the drive shaft 51 is connected to the rotary shaft of the motor main body 41. The drive shaft 51 is arranged on the channel 21 which extends inside the insertion section 16. The drive shaft 51, for example, is obtained by multi-layers of superimposing what is obtained by knitting metal wires in a cylindrical net shape, or is formed of multi-layer wires obtained by superimposing right winding wire rods and left winding wire rods, and has rotation flowability with respect to the motor main body 41.

On the distal end of the drive shaft 51 is provided the rotation gear 52. The rotation gear 52 is arranged in the cavity 34 of the base portion 33, and has its proximal end side attached to the drive shaft 51, and its distal end side attached to the base portion 33 via the support member 55, respectively. When a rotative force around a longitudinal axis is applied to the proximal end of the drive shaft 51, the drive shaft 51 rotates the rotation gear 52. On the outer periphery of the rotation gear 52 is arranged an internal gear 53 which covers the base portion 33 and is attached to the outer periphery thereof. The external teeth of the rotation gear 52 are meshed with the internal teeth of the internal gear 53. The internal gear 53 is rotatable with respect to the base portion 33 about a longitudinal axis which is a revolution axis. On the internal gear 53 is attached a shaft 56 of the internal roller 54.

When the driving force from the motor main body 41 of the driving source 40 is transmitted to the drive shaft 51, the rotation gear 52 rotates, and the internal gear 53 being meshed with the rotation gear 52 rotates (revolves) in a circumferential direction. When the internal gear 53 rotates in a circumferential direction, the internal roller 54 rotates (revolves) in a circumferential direction.

On the outer periphery of the insertion section 16, the internal gear 53 and the internal roller 54 are covered with a cover 60 which is a cover member with flexibility, such as being formed with rubber. In other words, the cover 60 is formed cylindrically around its axis. The cover 60 is fixed (for example, with a thread winding adhesion) to the base portion 33 by a cover fixing member 61 at both ends in the longitudinal axis direction. The cover 60 is a waterproof cover member which provides a barrier or a seal for protecting the internal gear 53, the internal roller 54, and other members arranged inside the insertion section 16 from the exterior environment (preventing intrusion of liquid from inside a body cavity, water, or other liquids), and configures an outer coat of the insertion section 16. The cover 60 allows maintaining the inside of the insertion section 16 of the endoscope 11 to be watertight.

Figure 5:
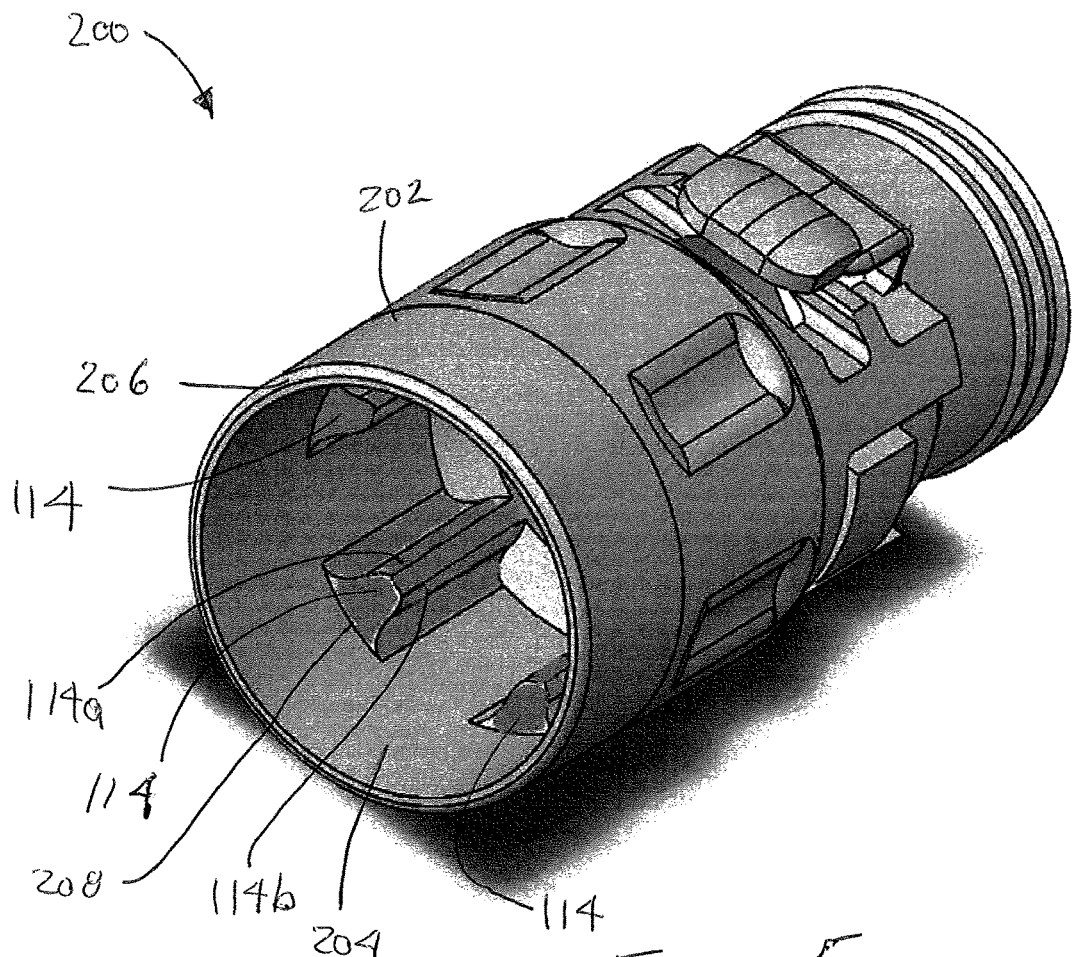
FIG. 5 illustrates a connector for use on an internal surface of the spiral tube of FIG. 1.

On the outside in the radial direction of the cover 60 is arranged a cam 114 corresponding to each internal roller 54 and which each engage a corresponding internal roller 54 to configure the driving force transmission mechanism 70. The cam 114 is provided on the inner periphery of the tube main body 110 which is attached to the outer periphery of the insertion section 16. The cam 114 can be integrally formed on the inner diameter of the tube main body or, as shown in FIG. 5, on a tubular connector 200 fixed to the inner diameter of the tube main body 110, such as by ultrasonic welding, adhesion, interference fit or the like. The tubular connector 200, and spiral tube 100 attached thereto, fit over the insertion section 16 as shown in FIG. 1.

As shown in FIG. 5, the connector 200 includes an exterior surface 202 that is fixed to an interior of the spiral tube 100 by methods known in the art, such as ultrasonic welding, adhesion and interference fit. The connector 200 also includes an internal bore 204 having the cams 114 projecting radially inward from the bore 204. The number of cams 114 matches the number of internal rollers 54. The cams 114 have cam surfaces 114a, 114b for engaging with the internal rollers 54. In a clockwise rotation direction of the spiral tube, one of the cam surfaces 114a, 114b engages with the internal rollers 54, while in the counterclockwise rotation direction of the spiral tube, the other of the cam surfaces 114a, 114b engages with the internal rollers 54.

The cams 114 can be integrally formed with the wall 206 of the connector 200 or formed separately therefrom and inserted in corresponding slots 208 formed in the wall 206. Such separately formed cams 114 can be fixed in the slots 208 by any methods known in the art, such as by insert molding, ultrasonic welding, adhesion or interference fit.

In FIG. 4, six internal rollers 54 and six cams 114 are arranged approximately in equal intervals on a circumference of the bore 204, and a state in which one internal roller 54 is in contact with one corresponding cam 114 with the cover 60 interposed therebetween as shown in FIG. 4. In other words, the inner periphery of the cover 60 is in contact with the internal rollers 54, and the outer periphery of the cover 60 is in contact with the cams 114.

When the driving source 40 is driven, the driving force is transmitted from the driving source 40 via the drive shaft 51, the rotation gear 52, and the internal gear 53, thereby, rotating (revolving) the internal roller 54 around the rotary axis A1 (revolution axis). The internal roller 54 rolls (rotates) on the cover 60 while the cams 114 slide on the cover 60. Since the cover 60 is fixed to the base portion 33 by the cover fixing members 61, the cover 60 does not rotate with respect to the insertion section 16. However, rotary motion of the internal gear 53 from the internal roller 54 is transmitted to the corresponding cam 114 which abuts the internal roller 54 via the cover 60. Accordingly, the driving force from the driving source 40 is transmitted to the spiral tube 100 from the driving force transmission mechanism 70 (the drive shaft 51, the rotation gear 52, the internal gear 53, the internal roller 54, the cover 60, and the cam 114), and the spiral tube 100 is rotated and driven around the rotary axis A1. For example, when observing curved organs such as the small intestine or the large intestine, the spiral tube 100 advances while pushing the wall of the intestinal wall abutting the spiral fin 112 of the rotating tube main body 110 to the proximal end side of the insertion section 16, and assists the insertion section 16 to be inserted deeply with the curved organ.

In this manner, the endoscope apparatus 1 is provided with the driving force transmission mechanism 70 for rotating the spiral tube 100 attached to the outer periphery of the insertion section 16 around the axis of the insertion section 16. The driving force transmission mechanism 70 comprises a first portion (the internal roller 54, or a bearing portion of the shaft 56 of the internal roller 54) which is connected to the driving source 40 and is moved in a circumferential direction about a predetermined axis (here, the longitudinal axis of the insertion section 16) by the driving force from the driving source 40. The driving force transmission mechanism 70 also comprises a second portion (the cam 114) which is capable of moving in the circumferential direction about the predetermined axis and is moved in the predetermined axial direction by coming in contact with the first portion when the first portion is moved. The cover 60 is arranged between the first portion and the second portion.

The material for the cam 114 should be selected to minimize the frictional drag on the driving source 40 and to minimize the torque required to operate the force transmission mechanism 70. To minimize wear on the cam 114 during use, as well as cumulative wear on the cover 60 of the endoscope, a material can be selected for the cam 114 to minimize friction and wear properties. However, mechanical integrity and assembly must also be considered for the selected material. For example, a material from the fluoropolymer group, or low friction polyester group can be selected. Such materials, such as HDPE, can balance all of the above requirements for the cams 114 as well as for other portions of the spiral tube 100 or connector 200. In one configuration, the spiral tube 100 can be formed of LDPE, while the connector 200 can be formed of HDPE, which enables the connector 200 to be ultrasonically welded to the spiral tube 100. Such materials also provide for a proper pawl 113 engagement for locking the spiral tube 100 and connector 200 to the groove 38 of the endoscope.

The integral cams 114 of the spiral tube 100 or connector 200 can be molded and eliminate the cost of conventional machined steel roller bearings, a precision molded bearing retaining collar, as well as the part inspection, and assembly time. Furthermore, the transmission efficiency is comparable to the conventional bearing design, and as discussed above, results in a large reduction in component, assembly and inspection costs.

Figure 6A:
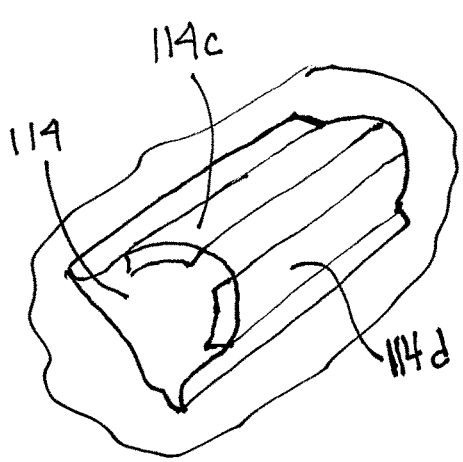
FIGS. 6a and 6b illustrate other embodiments of the cam surfaces of FIG. 4.

As discussed above with regard to FIG. 5, the exterior cams 114 can be formed separately from the wall 206 of the connector 200, which can be a different material than the material of the connector 200. Alternatively, as shown in FIG. 6a, only the cam surfaces 114a, 114b of the internal cams 114 that contact with the cover 60 can employ another material 114c, 114d having a lower friction and/or greater wear properties while requirements for other portions of the spiral tube 100 or connector 200 can be maximized, such as employing less expensive materials, easier to manufacture tolerances and/or materials and/or stronger materials. The spiral tube 100 or connector 200 requires rigidity in the locking configuration such as at pawl 113 to ensure retention on the spiral tube 100 on the mating groove 38 of the insertion section under tensile loads. In this case, a material such as a high strength engineering polymer or reinforced polymer can be used. However, such materials tend to have poor frictional properties required for the cams 114 on the spiral tube 100 or on the connector 200.

A material having a lower friction and/or greater wear used for the cams 114, or, as is shown in FIG. 6a, for only the cam surfaces 114a, 114b can have a different material 114c, 114d different from other portions of the cams 114. Such materials can be selected from the fluoropolymer group, or low friction polyester group and can be formed at the cam surfaces 114a, 114b of the cams 114 by any methods known in the art, such as a two shot or insert molding process to differentiate the cams 114 and/or the cam surfaces 114a, 114b from the remaining portions of the spiral tube 100 or connector 200, thus enabling a preferred material at the friction point while maintaining a desired material for other portions. The different materials 114c, 114d for the cam surfaces 114a, 114b may also be snapped in place, ultrasonically welded or pressed with an interference fit.

Figure 6B:
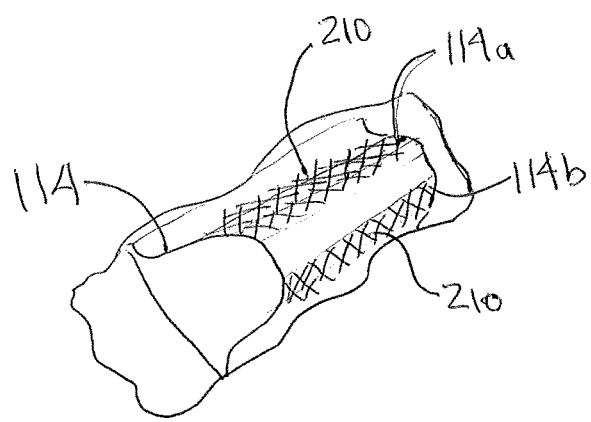

In addition, as shown in FIG. 6b, a surface texture and/or pattern 210 can be added to the cam surfaces 114a, 114b to hold a lubricant film between the cam surface and the cover 60. This may be achieved with conventional mold finish techniques or post molding embossing. Such surface texture and/or pattern 210 may be used on the above described inserts or on the cam surface materials 114c, 114d of integrally formed cams 114 with the remaining portions of the spiral tube 100 or connector 200.

In another embodiment, the cam surface 114a, 114b may be porous and infused with a water soluble lubricant to be eluded during exposure to water while in use. This porosity can be created by additive manufacturing methods by way of example.

While there has been shown and described what is considered to be preferred embodiments, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A spiral tube for use with an endoscope insertion section having a rotating member, the spiral tube comprising:
    a tube; and
    a spiral fin disposed on an exterior surface of the tube;
    wherein an inner cylindrical surface of the tube having a plurality of cylindrical portions, each of the plurality of cylindrical portions having a partial cylindrical surface extending in a circumferential direction of the inner cylindrical surface and a plurality of cams circumferentially spaced between each of the plurality of cylindrical portions to project radially inward from an inner cylindrical surface of the tube, the plurality of cams extending in a longitudinal direction of the tube;
    wherein each of the plurality of cams are configured to be movable relative to the rotating member when the tube is mounted on the endoscope insertion section and each of the plurality of cams have one or more cam surfaces configured to engage the rotating member to rotate the spiral tube; and
    the one or more cam surfaces are fixed relative to the inner cylindrical surface of the tube.

2. The spiral tube of claim 1, wherein the tube further comprising a tubular connector fixed to the tube and forming the inner cylindrical surface of the tube, the tubular connector having the plurality of cams.

3. The spiral tube of claim 2, wherein the plurality of cams are formed of a material different from a material forming other portions of the tubular connector.

4. The spiral tube of claim 2, wherein at least the one or more cam surfaces of the plurality of cams are configured to be coated with a material different from a material forming other portions of the tubular connector.

5. The spiral tube of claim 2, wherein at least the one or more cam surfaces of the plurality of cams are configured to be formed of a material different from a material forming other portions of the plurality of cams.

6. An endoscope system comprising:
    an endoscope having an elongated insertion section, the insertion section having a rotating member;
    a spiral tube rotatably disposed on the insertion section, the spiral tube comprising:
        a tube; and
        a spiral fin disposed on an exterior surface of the tube;
        wherein an inner cylindrical surface of the tube having a plurality of cylindrical portions, each of the plurality of cylindrical portions having a partial cylindrical surface extending in a circumferential direction of the inner cylindrical surface and a plurality of cams circumferentially spaced between each of the plurality of cylindrical portions to project radially inward from an inner cylindrical surface of the tube, the plurality of cams extending in a longitudinal direction of the tube;
    wherein each of the plurality of cams have one or more cam surfaces configured to engage the rotating member to rotate the spiral tube; and
    the one or more cam surfaces are fixed relative to the inner cylindrical surface of the tube and the rotating member is movable relative to the one or more cam surfaces.

7. The endoscope system of claim 6, wherein the tube further comprising a tubular connector fixed to the tube and forming the inner cylindrical surface of the tube, the tubular connector having the plurality of cams.

8. The endoscope system of claim 7, wherein the plurality of cams are formed of a material different from a material forming other portions of the tubular connector.

9. The endoscope system of claim 7, wherein at least the one or more cam surfaces of the plurality of cams are configured to be coated with a material different from a material forming other portions of the tubular connector.

10. The endoscope system of claim 7, wherein at least the one or more cam surfaces of the plurality of cams are configured to be formed of a material different from a material forming other portions of the plurality of cams.

11. The endoscope of claim 1, wherein the one or more cam surfaces are each curved surfaces.

12. The endoscope system of claim 6, wherein the rotating member is a plurality of rollers.

13. The endoscope system of claim 6, wherein each of the plurality of rollers corresponds to a respective one of the plurality of cams.

14. The endoscope system of claim 6, wherein:
    the one or more cam surfaces comprises a first cam surface and a second cam surface, the first cam surface being configured to movably engage the rotating member to rotate the spiral tube in a clockwise direction and the second cam surface being configured to movably engage the rotating member to rotate the spiral tube in a counterclockwise direction; and
    the first cam surface and the second cam surface are each fixed relative to the inner cylindrical surface of the tube.

15. The endoscope of claim 14, wherein the first cam surface and the second cam surface are each curved surfaces.

* * * * *